(12) United States Patent
Dürst et al.

(10) Patent No.: US 6,388,065 B1
(45) Date of Patent: May 14, 2002

(54) DNA FOR EVALUATING THE PROGRESSION POTENTIAL OF CERVICAL LESIONS

(75) Inventors: Matthias Dürst, Naumann Str. (DE); Matthias Nees, Rockville, MD (US)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/308,984

(22) PCT Filed: Nov. 12, 1997

(86) PCT No.: PCT/DE97/02660

§ 371 Date: Sep. 3, 1999

§ 102(e) Date: Sep. 3, 1999

(87) PCT Pub. No.: WO98/23775

PCT Pub. Date: Jun. 4, 1998

(30) Foreign Application Priority Data

Nov. 27, 1996 (DE) .......................................... 196 49 207

(51) Int. Cl.[7] ........................ C07H 21/04; C07H 21/02; C12Q 1/68; C12P 19/34; C12P 21/06
(52) U.S. Cl. .......................... 536/23.5; 536/23.1; 435/6; 435/91.2; 435/69.1; 436/64
(58) Field of Search ............................... 536/23.1, 23.5; 435/6, 7.1, 7.21, 7.23, 320.1, 325, 69.1, 91.2; 436/64

(56) References Cited

U.S. PATENT DOCUMENTS 5,532,348 A * 7/1996 Huibregste et al. ........ 536/23.5

OTHER PUBLICATIONS

Barnes et al., Gynecologic Oncology, vol. 38, pp. 343–346, 1990.*
Lazar et al., Molecular and Cellular Biology, vol. 8, No. 3, pp. 1247–1252, Mar. 1988.*
Burgess et al., The Journal of Cell Biology, vol. 111, pp. 2129–2138, Nov. 1990.*
Bowie et al., Science, Vol. 247, pp. 1306–1310, Mar. 1990.*
Bork, Genome Research, vol. 10, pp. 398–400, 2000.*

* cited by examiner

Primary Examiner—Sheela Huff
Assistant Examiner—Jennifer Hunt
(74) Attorney, Agent, or Firm—Fulbright & Jaworski L.L.P.

(57) ABSTRACT

The present invention relates to a nucleic acid which is suitable for evaluating the progression potential of cervial lesions, wherein the nucleic acid is obtainable by a process in which RNA from early and late passages of HPV-immortalized cells is isolated and the RNAs characteristic for the early passages and late passages, respectively, are identified and provided as DNA or RNA. Furthermore, the present invention concerns polypeptides coded by such a nucleic acid. In addition, it covers antibodies directed against the polypeptides. Moreover, it relates to the use of the DNA and the polypeptides as well as a kit suitable for evaluating the progression of cervical lesions.

4 Claims, 2 Drawing Sheets

```
        GCAATCGATGGGGCATCCTTTCTGAAGATCTTCGGGCCACTGTCGTCCAGTGCCATGCAG
   1    ---------+---------+---------+---------+---------+---------+   60
        CGTTAGCTACCCCGTAGGAAAGACTTCTAGAAGCCCGGTGACAGCAGGTCACGGTACGTC a       A  I  D  G  A  S  F  L  K  I  F  G  P  L  S  S  S  A  M  Q   -

TTTGTCAACGTGGGCTACTTCCTCATCGCAGCCGGCGTTGTGGTCTTTGCTCTTGGTTTC
  61    ---------+---------+---------+---------+---------+---------+  120
        AAACAGTTGCACCCGATGAAGGAGTAGCGTCGGCCGCAACACCAGAAACGAGAACCAAAG a       F  V  N  V  G  Y  F  L  I  A  A  G  V  V  V  F  A  L  G  F   -

CTGGGCTGCTATGGTGCTAAGACTGAGAGCAAGTGTGCCCTCGTGACGTTCTTCTTCATC
 121    ---------+---------+---------+---------+---------+---------+  180
        GACCCGACGATACCACGATTCTGACTCTCGTTCACACGGGAGCACTGCAAGAAGAAGTAG a       L  G  C  Y  G  A  K  T  E  S  K  C  A  L  V  T  F  F  F  I   -

CTCCTCCTCATCTTCATTGCTGAGGTTGCAGCTGCTGTGGTCGCCTTGGTGTACACACTA
 181    ---------+---------+---------+---------+---------+---------+  240
        GAGGAGGAGTAGAAGTAACGACTCCAACGTCGACGACACCAGCGGAACCACATGTGTGAT a       L  L  L  I  F  I  A  E  V  A  A  A  V  V  A  L  V  Y  T  I   -

ATGGCTGAGCACTTCCCGACGTTGCTGGTAGTGCCTGCCATCAAGAAGATTATGGTT
 241    ---------+---------+---------+---------+--------+-------  297
        TACCGACTCGTGAAGGGCTGCAACGACCATCACGGACGGTAGTTCTTCTAATACCAA a       M  A  E  H  F  P  T  L  L  V  V  P  A  I  K  K  I  M  V   -
```

FIG. 1

```
    GCAATCGATGGGGCATCCTTTCTGAAGATCTTCGGCCACTGTCGTCCAGTGCCATGCAG
1   ---------+---------+---------+---------+---------+---------+   60
    CGTTAGCTACCCCGTAGGAAAGACTTCTAGAAGCCGGTGACAGCAGGTCACGGTACGTC

A  I  D  G  A  S  F  L  K  I  F  G  P  L  S  S  S  A  M  Q

TTTGTCAACGTGGGCTACTTCCTCATCGCAGCCGGCGTTGTGGTCTTTGCTCTTGGTTTC
61  ---------+---------+---------+---------+---------+---------+   120
    AAACAGTTGCACCCGATGAAGGAGTAGCGTCGGCCGCAACACCAGAAACGAGAACCAAAG

F  V  N  V  G  Y  F  L  I  A  A  G  V  V  F  A  L  G  F

CTGGGCTGCTATGGTGCTAAGACTGAGAGCAAGTGTGCCCTCGTGACGTTCTTCTTCATC
121 ---------+---------+---------+---------+---------+---------+   180
    GACCCGACGATACCACGATTCTGACTCTCGTTCACACGGGAGCACTGCAAGAAGAAGTAG

L  G  C  Y  G  A  K  T  E  S  K  C  A  L  V  T  F  F  F  I

CTCCCTCCTCCATCTTCATTGCTGAGGTTGCAGCTGCTGTGGTCGCCTTGGTGTACACACTA
181 ---------+---------+---------+---------+---------+---------+   240
    GAGGAGGAGTAGAAGTAACGACTCCAACGTCGACGACACCAGCGAACCACATGTGTGTAT

L  L  L  I  F  I  A  E  V  A  A  A  V  V  A  L  V  Y  T  I

ATGGCTGAGCACTTCCCGACGTTGCTGGTAGTGCCTGCCATCAAGAAGATTATGGTT
241 ---------+---------+---------+---------+---------+------       297
    TACCGACTCGTGAAGGGCTGCAACGACCATCACGGACGGTAGTTCTTCTAATACCAA

```
  1  AGCCAGCGAA CGGACGAGGG TGACAATAGA GTGTGGTGTC ATGCTTGTGA
 51  GAGAGAAAAC ACTTTCGAGT GCCAGAACCC AAGGAGGTGC AAATGGACAG
101  AGCCATACTG CGTTATAGCG GCCGTGAAAA TATTTCCACG TTTTTTCATG
151  GTTGCGAACA GGTGCTCCGC TGGTTGTGCA GCGATGGAGA GACCCAAGCC
201  AGAGGAGAAG CGGTTTCTCC TGGAAGAGCC CATGCCCTTC TTTTACCTCA
251  AGTGTTGTAA A
```

DNA FOR EVALUATING THE PROGRESSION POTENTIAL OF CERVICAL LESIONS

This invention relates to nucleic acid molecules suitable for evaluating the progression potential of cervical lesions, and to polypeptides encoded by such a nucleic acid molecules. Furthermore, this invention concerns antibodies directed against the polypeptides. Moreover, it covers the use of the nucleic acid molecules and the polypeptides as well as a kit suitable for evaluating the progression of cervical lesions.

Invasive cervical carcinoma usually follows from a precancerosis. Precanceroses cover a wide range of lesions referred to as mild to severe dysplasias (CIN1 to CIN3) pertaining to histopathology. CIN1 lesions frequently regress spontaneously and usually need not be treated. On the other hand, these lesions can persist over years or change into a more severe lesion, e.g. CIN3, or into a microinvasive carcinoma. A cytological method has been used for the diagnosis of cervical smears for about 50 years, by means of which dysplastic cells can be detected in cervical smears. This method is generally known as the "Pap test". The "Pap test" contributed to the fact that the incidence of the cervical carcinoma could be reduced significantly in the past.

Several years ago, it was also found that the presence of dysplastic lesions and cervical carcinomas correlates with the detection of cervical carcinoma-associated human papilloma viruses, e.g. HPV 16 or HPV 18. The detection of antibodies against the viral HPV oncoproteins E6 and E7 in patient serum by means of ELISA or comparable methods is also possible as a detection of premalignant or malignant cervical diseases. It is also known that certain chromosomal deletions are associated with an increased risk of malignant transformation of the corresponding precancerosis. Morphological changes of cells and cell nuclei also correlate with malignant progression. These changes can be detected by means of cytometry.

Nevertheless, it is not possible by either the "Pap test" or the detection of oncogenic HPV types to make a prognosis regarding the further development of individual lesions. This also applies to the detection of HPV-specific antibodies in patient serum. By means of this serological method it is rather only possible to detect patients who already suffer from a carcinoma. Therefore, the antibody detection method cannot be considered a supplement to the present precaution but only to the manifestation of the finding that a carcinoma has developed already. In addition, the genetical analyses and cytometric approaches include the drawback that they are technically very complicated and therefore are not useful for routine diagnostics.

Therefore, it is the object of the present invention to provide a product by which the progressive potential of cervical lesions can be evaluated reliably.

This is the subject of the invention set forth in the disclosure which follows.

Thus, the subject matter of the present invention relates to an isolated nucleic acid molecule suitable for evaluating the progressive potential of cervical lesions. Such a nucleic acid molecule can be obtained by common methods. A method is preferred in which RNA from early and late passages of HPV-immortalized cells is isolated and the RNAs characteristic of the early passages and late passages, respectively, and expressed in markedly differing amounts, respectively, are identified and provided as DNA or RNA.

The present invention is based on the applicant's finding that late passages of HPV-immortalized cells cause tumors in naked mice, whereas early passages of such cells are not capable of doing so. The inventor also discovered that in late passages of HPV-immortalized cells certain RNAs are detected more strongly than is the case in early passages of such cells.

For the provision of a nucleic acid according to the invention RNA from early and late passages of HPV-immortalized cells are isolated. Early passages are e.g. passages 20–60, and late passages start from e.g. 130. For example, HPV 16-immortalized, human preputial keratinocytes, HPK-IA cells can be used as cells (cf. Dürst, M. et al., Oncogene 1/3 (1987), 251–256). The RNA of the early and late passages can be compared with each other and differences can be determined which are characteristic of the early passages and late passages, respectively. To this end, it is favorable to subject the RNA to reverse transcription. In this case, it is advantageous to use what are known as another primers, i.e. oligo-d(T) primers which following a sequence of 11–15 thymidine bases have two more bases at the 3' end and thus recognize in well-known fashion the transition from the 3' end of an mRNA to the poly-A tail where they bind. The resulting cDNA can be subjected to amplification in a PCR method. For this purpose, it is favorable to use common "arbitrary" primers together with the above anchor primers. The amplified cDNA can then be subjected to denatured polyacrylamide gel electrophoresis. In this step, cDNA bands are identified which have a differing intensity in the cDNA samples to be compared with one another, i.e. RNA isolates from the early and late passages of HPV-immortalized cells. These cDNA bands can be isolated from the gel and subjected to another round of amplification. Moreover, they can be cloned and their sequences can be determined. A person skilled in the art is familiar with the above methods. By way of supplement reference is made to the following literature (cf. Liang et al., Cancer Research 52, (1992), 6966–6968; Liang et al., Science 257, (1992), 967–971; Liang et al., Nucleic Acids Research 21, (1993), 3269–3275).

Both cDNA and RNA are examples of nucleic acid molecules in accordance with the invention, with cDNA. A (c)DNA which comprises a base sequence of FIG. 1 or FIG. 2 or a sequence differing therefrom by one or several base pairs is particularly preferred. The (c)DNA of FIG. 1 was deposited as C4.8 with the DSMZ (Deutsche Sammlung von Miroorganismen und Zellkulturen) [Germany-type collection of microorganisms and cell cultures] under DSM 11197 on Oct. 4, 1996. Furthermore, the (c)DNA of FIG. 2 was deposited as C21.7 with the DSMZ under DSM 11198 on Oct. 4, 1996. A nucleic acid molecule according to the invention is described as DNA by way of example below.

A DNA according to the invention can be present in a vector or an expression vector, respectively. The person skilled in the art is familiar with examples thereof. In the case of an expression vector for *E. coli* these include e.g. pGEMEX, pUC derivatives, pGEX-2T, pQE-8 and pet3d. For the expression in yeast e.g. pY100 and Ycpad1 have to be mentioned, while e.g. PKCR, pEFBOS, cDM8 and pCEV4 have to be indicated for the expression in animal cells. The baculovirus expression vector pAcSGHisNT-A is particularly suitable for the expression in insect cells.

The person skilled in the art knows suitable cells which express DNA according to the invention, which is present in an expression vector. Examples of such cells comprise the *E. coli* strains HB101, DH1, x1776, JM101, JM109, SG13009 and BL21, the yeast strain *Saccharomyces cerevisiae* and the animal cells L, 3T3, FM3A, CHO, COS, Vero and HeLa as well as the insect cells sf9.

The person skilled in the art knows in which way a DNA according to the invention has to be inserted in an expression vector. He is also familiar with the fact that this DNA can be inserted in combination with a DNA coding for another polypeptide, so that the DNA according to the invention can be expressed in the form of a fusion protein.

In addition, the person skilled in the art knows conditions of culturing transformed cells and transfected cells, respectively. He is also familiar with methods of isolating and purifying the polypeptide expressed by the DNA according to the invention. Thus, such a polypeptide, which may also be a fusion polypeptide, also represents a feature of the present invention. A polypeptide in accordance with the invention preferably comprises the amino acid sequence of FIG. 1 or a sequence differing therefrom by one or several amino acids.

A further aspect of the present invention relates to an antibody directed against an above polypeptide and fusion polypeptide, respectively. Such an antibody can be prepared by common methods. It may be polyclonal an monoclonal, respectively. For its preparation it is favorable to immunize animals—particularly rabbits or chickens for a polyclonal antibody and mice for a monoclonal antibody—with an above (fusion) polypeptide. Further "boosters" of the animals can be effected with the same (fusion) polypeptide. The polyclonal antibody can then be obtained from the animal serum and egg yolk, respectively. For the preparation of the monoclonal antibody, animal spleen cells are fused with myeloma cells.

The present invention enables the reliable evaluation of the progressive potential of cervical lesions. By means of an antibody according to the invention it can be determined whether cervical smears contain polypeptides which are characteristic of early or late passages of HPV-immortalized cells. Furthermore, it is possible to detect an autoantibody directed against the polypeptide present in the body by means of a polypeptide according to the invention. Both detections can be made by common methods, particularly a Western blot, an ELISA, an immunoprecipitation or by immunofluorescence. In addition, it is possible by means of a nucleic acid molecule according to the invention, particularly DNA and primers derived therefrom, to detect whether RNA which is characteristic of early or late passages of HPV-immortalized cells is present in cervical smears. This detection can be made in accordance with known methods, particularly in a Southern blot. By means of the present invention it is thus possible, to make an early diagnosis of whether a cervical carcinoma is forming.

Furthermore, the present invention is useful for preventing formation of a cervical carcinoma. By means of an antibody according to the invention it is possible to inhibit a polypeptide which is characteristic of late passages of HPV-immortalized cells. Moreover, a nucleic acid molecule according to the invention, particularly DNA, can be used to inhibit such a polypeptide. To this end, the nucleic acid molecule is used for the inhibition of expression of the gene coding for the polypeptide, e.g. as a basis of preparing anti-sense oligonucleotides.

To carry out the invention, particularly as regards the diagnostic aspect, a kit is also provided. It contains one or several nucleic acid molecules polypeptides and/or antibodies according to the invention. In particular, it comprises those nucleic acid molecules and/or polypeptides which are said to be preferred above. In addition, the kit contains conventional excipients such as carriers, buffers, solvents and controls. The kit is also the subject matter of the present invention.

The present invention is explained by the examples which follow.

BRIEF DESCRIPTION OF THE DRAWINGS

FIG. 1 shows the base sequence of (c)DNA C4.8 according to the invention. In addition, the amino acid sequence of the polypeptide encoded by (c)DNA C4.8 is indicated, FIG. 2 shows the base sequence of (c)DNA C21.7 according to the invention.

EXAMPLE 1

Preparation of cDNAS C4.8 and C21.7 According to the Invention

Whole RNA was isolated in each case by the known guanidine thiocyanate (GTC) method from early passages, i.e. passage p49, and late passages, i.e. passage p359 and p389, of the HPV-immortalized cell line HPK-IA. The whole RNA was subjected to a conventional DNase reaction, using commercially available, RNase-free DNase purchased from PROMEGA.

The resulting DNase-free whole RNA was subjected to as reverse transcription, using another primers, as are described supra. Following a sequence of 11–15 thymidine bases, these primers have two more bases at the 3' end, e.g. AA, AC, AG, CA, CC, CG, GA, GC, GG, AT, CT, GT, so that the primers are bound directly at the transition from the mRNA to the poly-A tail.

The conditions for reverse transcription were as follows:

| | |
|---|---|
| RNasine 20 u/µl | 1.0 µl |
| dNTP-Mix (2.5 mM) | 1.2 µl |
| MMLV reverse transcriptase 300 u/µl | 2.5 µl |
| 0.1 M DTT | 5.0 µl |
| whole RNA 250 ng/µl | 5.0 µl |
| T$_{12}$VV primers (V = A, C or G), 25 µM | 5.0 µl |
| 5 × RT buffer | 10.0 µl |
| dH$_2$O | 20.3 µl |
| | 50.0 µl |

*5 × RT buffer:
250 mM Tris-HCl (pH 7.6)
375 mM KCl
15 TnM MgCl$_2$

The whole RNA was denatured prior to the reaction at 70–80° C. for 5 minutes, then quenched on ice and fed to the reaction vessel. All of the other components were mixed at 0° C. and added to the whole RNA. Ultimately all was coated with mineral oil and incubated in a water bath at 37° C. for 45–60 minutes. Finally, the reaction was stopped by inactivating the enzyme at 95° C. (5 minutes). Having terminated the reaction, the RT batches were frozen at −20° C. up to their use.

The resulting cDNA was subjected to a PCR method. To this end, 20 µl batches were made, each having 2 µl of the above reverse transcription batch as template (1/10 of the reaction volume, corresponding to the equivalent of 25–50 ng cDNA/PCR batch). The other components (cf. below) were prepared as "master mix" and then added. A PCR reaction batch was composed as follows:

| | |
|---|---|
| RT batch (prepared) | 2.0 µl |
| Mix: | |
| 10 × PCR buffer* | 2.0 µl |
| 10-mer arbitrary primer 5 µM | 2.0 µl |
| T$_{12}$VV primer (V = A, C or G), 25 µM | 2.0 µl |
| dNTP mix (2.5 mM in toto) | 0.4 µl |
| 50 mM MgCl$_2$ | 0.7 µl |

-continued

| Taq DNA polymerase 20 U/μl | 0.2 μl |
| α-$^{32}$P-dCTP | 0.1 μl |
| dH$_2$O | 10.6 μl |
| | 20.0 μl |

10 × PCR buffer:
200 mM Tris-HCl (pH 8.55)
160 mM (NH$_4$)$_2$SO$_4$
magnesium: optimum concentration is adjusted with 50 mM MgCl$_2$ The 10-mer arbitrary primer is e.g. "AGC CAG CGA A" (AP-1) or "GCA ATC GAT G" (AP-6). The reaction was carried out in a DNA thermocycler (Perkin-Elmer Gen-Amp 9600) with the following program steps:

| Program 1: | denaturation | 95° C., 3 minutes | 1 cycle |
| Program 2: | denaturation | 95° C., 15 seconds | a maximum |
| | primer annealing | 40° C., 12 minutes | of 30 |
| | primer extension | 72° C., 30 seconds | cycles |
| Program 3: | primer extension | 72° C., 5 minutes | 1 cycle |

Having terminated the PCR method, the batches were applied to a denaturing 4.5–6% polyacrylamide gel. By comparing the cDNA bands from the early and late passages of the HPK-IA cells, those could be identified which were different, i.e. were represented in the late passages much more than in the early ones.

These cDNA bands were used for another amplification. To this end, they were cut out of the polyacrylamide gel and used in another PCR method. The PCR batch was composed as follows:

| 10 × PCR buffer | 5.0 μl |
| 10-mer arbitrary primer 5 μM | 5.0 μl |
| T$_{12}$VV primer (V = A, C or G), 25 μM | 5.0 μl |
| dNTP mix (25 mM in toto) | 1.2 μl |
| 50 mM MgCl$_2$ | 1.5 μl |
| Taq-DNA polymerase 20 U/μl | 1.0 μl |
| dH$_2$O | 31.5 μl |
| | 50.0 μl |

The PCR reaction was carried out under the same conditions and with the same program sequence as the first PCR reaction.

Having terminated the PCR reaction, the batches were separated on a 1% agarose gel, and the desired DNA bands were cut out of the gel. Thereafter, the DNA bands were eluted from the agarose pieces by using what is called "GenElute" columns (SUPELCO company).

The resulting cDNA was cloned into the cloning vector pCRII using the "TA cloning kit" (INVITROGEN company). Resulting clones were sequenced by means of the "T7 sequencing kit" (PHARMACIA company). The cDNAs C4.8 and C21.7 according to the invention were obtained.

EXAMPLE 2

Comparative Studies Using cDNAs C4.8 and C21.7 According to the Invention a) The whole RNA isolated according to Example 1 from early and late passages of HPK-IA cells was subjected to a denaturing 4.5–6% polyacrylamide gel electrophoresis. Thereafter, a conventional Northern blot was carried out, the RNA being transferred to "Gene Screen-Plus" nylon membranes. $^{32}$P-labeled cDNAs C4.8 and C21.7 according to the invention were used for hybridization.

The results indicated that the cDNAs according to the invention react much more strongly with the RNA from the late passages of the HPK-IA cells than was the case with the early passages.

b) Furthermore, RNA-RNA in situ hybridizations were made with freezing sections from cervical tissues, namely normal epithelial tissue, premalignant lesion and carcinoma to evaluate the condition of the tissue. RNA probes were used as hybridization probes, which were obtained from the cDNAs C4.8 and C21.7 according to the invention. To this end, the latter were linearized and RNA was synthesized by adding the corresponding RNA polymerase, preferably SP6 or T7, and $^{32}$P rUTP. The RNA-RNA in situ hybridization with the above tissue was carried out under stringent conditions, e.g. at 60° C.

It turned out that strong hybridization was only obtained in connection with the cervical carcinoma.

However, the hybridization was very low in the case of normal epithelial tissue.

The above data underline that the present invention is perfectly suited to detect potentially malignant cells in a cervical smear.

SEQUENCE LISTING

<160> NUMBER OF SEQ ID NOS: 4

<210> SEQ ID NO 1
<211> LENGTH: 297
<212> TYPE: DNA
<213> ORGANISM: Homo sapiens

<400> SEQUENCE: 1

```
gca atc gat ggg gca tcc ttt ctg aag atc t tc ggg cca ctg tcg tcc    48
Ala Ile Asp Gly Ala Ser Phe Leu Lys Ile P he Gly Pro Leu Ser Ser
1               5                   10                  15 agt gcc atg cag ttt gtc aac gtg ggc tac t tc ctc atc gca gcc ggc    96
Ser Ala Met Gln Phe Val Asn Val Gly Tyr P he Leu Ile Ala Ala Gly
```

```
                    20                  25                  30
gtt gtg gtc ttt gct ctt ggt ttc ctg ggc t gc tat ggt gct aag act        144
Val Val Val Phe Ala Leu Gly Phe Leu Gly C ys Tyr Gly Ala Lys Thr
            35                  40                  45 gag agc aag tgt gcc ctc gtg acg ttc ttc t tc atc ctc ctc atc            192
Glu Ser Lys Cys Ala Leu Val Thr Phe Phe P he Ile Leu Leu Ile
    50                  55                  60 ttc att gct gag gtt gca gct gct gtg gtc g cc ttg gtg tac acc ata        240
Phe Ile Ala Glu Val Ala Ala Ala Val Val A la Leu Val Tyr Thr Ile
65                  70                  75                  80 atg gct gag cac ttc ccg acg ttg ctg gta g tg cct gcc atc aag aag        288
Met Ala Glu His Phe Pro Thr Leu Leu Val V al Pro Ala Ile Lys Lys
                85                  90                  95 att atg gtt                                                             297
Ile Met Val <210> SEQ ID NO 2
<211> LENGTH: 261
<212> TYPE: DNA
<213> ORGANISM: Homo sapiens

<400> SEQUENCE: 2
agccagcgaa  cggacgaggg  tgacaataga  gtgtggtgtc  atgcttgtga  g agagaaaac      60 actttcgagt  gccagaaccc  aaggaggtgc  aaatggacag  agccatactg  c gttatagcg     120 gccgtgaaaa  tatttccacg  ttttttcatg  gttcgcaaca  ggtgctccgc  t ggttgtgca     180 gcgatggaga  gacccaagcc  agaggagaag  cggtttctcc  tggaagagcc  c atgcccttc     240 ttttacctca  agtgttgtaa  a                                                   261

<210> SEQ ID NO 3
<211> LENGTH: 10
<212> TYPE: DNA
<213> ORGANISM: Homo sapiens

<400> SEQUENCE: 3
agccagcgaa                                                                   10

<210> SEQ ID NO 4
<211> LENGTH: 10
<212> TYPE: DNA
<213> ORGANISM: Homo sapiens

<400> SEQUENCE: 4
gcaatcgatg                                                                   10
```

What I claimed is:

1. An isolated nucleic acid molecule which encodes the protein encoded by SEQ ID NO: 1.

2. The isolated nucleic acid molecule of claim 1, comprising the nucleotide sequence of SEQ ID NO: 1.

3. An isolated nucleic acid molecule useful in determining progression of a cervical lesion, comprising the nucleotide sequence of SEQ ID NO: 2.

4. A method for determining progression of a cervical lesion, comprising determining expression or level of expression of a nucleic acid molecule which either (i) encodes the protein encoded by the nucleotide sequence set forth in SEQ ID NO: 1, or (ii) comprises the nucleotide sequence of SEQ ID NO: 2, in a sample of HPV immortalized cells taken from said cervical lesion, and correlating said determination to a predetermined level of expression indicative of status of a cervial cancer lesion.

* * * * *